United States Patent [19]

Kuznetz

[11] 4,425,917

[45] Jan. 17, 1984

[54] HEAT EXCHANGE SYSTEM FOR BODY SKIN

[76] Inventor: Lawrence Kuznetz, 12214 Lakewood Blvd., Downey, Calif. 90241

[21] Appl. No.: 261,460

[22] Filed: May 7, 1981

[51] Int. Cl.³ .............................................. A61F 7/00
[52] U.S. Cl. .................................... 128/403; 128/399
[58] Field of Search ............................... 128/403, 399

[56] References Cited

U.S. PATENT DOCUMENTS

| | | | |
|---|---|---|---|
| 3,612,059 | 10/1971 | Ersek | 128/399 |
| 3,822,705 | 7/1974 | Pilotte | 128/403 |
| 3,889,684 | 6/1975 | Lebold | 128/403 |
| 4,044,773 | 8/1977 | Baldwin | 128/403 |
| 4,204,543 | 5/1980 | Henderson | 128/403 |
| 4,326,533 | 4/1982 | Henderson | 128/403 |

*Primary Examiner*—C. Fred Rosenbaum
*Assistant Examiner*—C. W. Shedd

*Attorney, Agent, or Firm*—Michael Ebert

[57] ABSTRACT

A heat exchange system for personal use to provide beneficial cooling or warming effects, depending on the operating mode of the system. Included is a supply of replaceable thermal cartridges, each of which is insertable in a fabric holder having wicking properties, the loaded holder or thermal assembly being adapted to engage and conform to a skin area on the individual that is subject to sweating, such as the brow or neck. Each cartridge is constituted by a sealed flexible envelope formed of plastic film, preferably having a metallic layer thereon acting to reflect radiant energy. The envelope encloses a gel or liquid having a high heat capacity whereby when the supply of cartridges is pre-heated or refrigerated, each cartridge is thereby activated. When an activated cartridge is placed in the holder to engage the skin of an individual, it then functions either as a heat sink or heat source with respect thereto.

14 Claims, 11 Drawing Figures

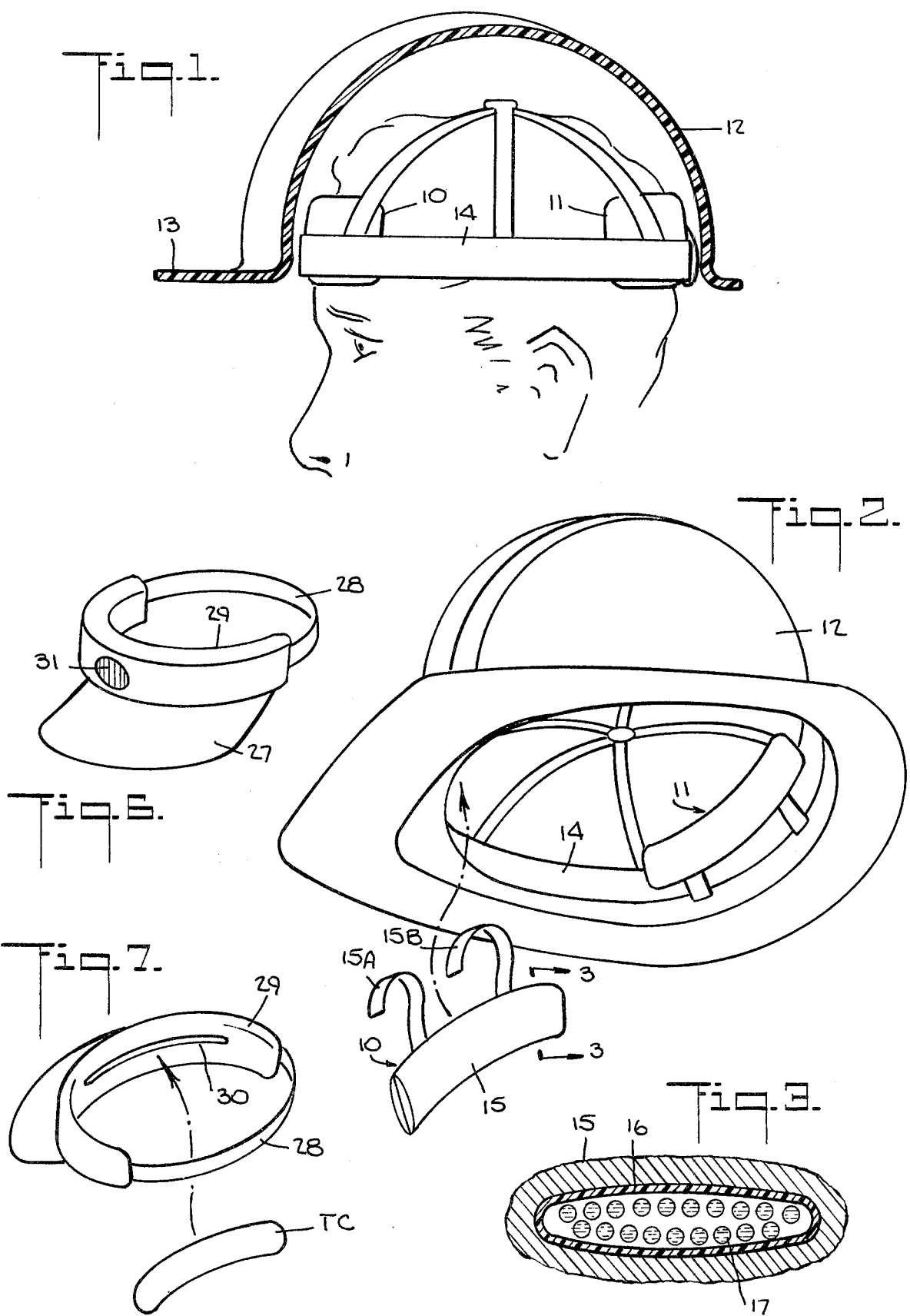

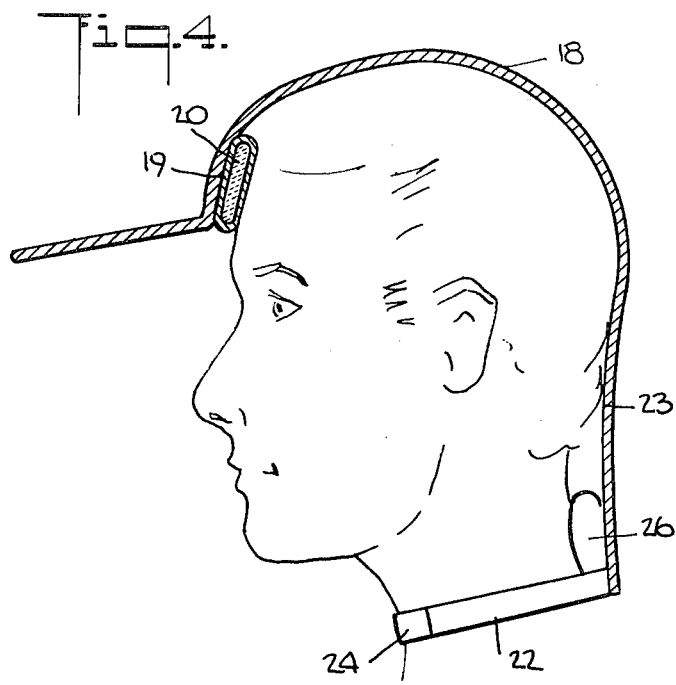
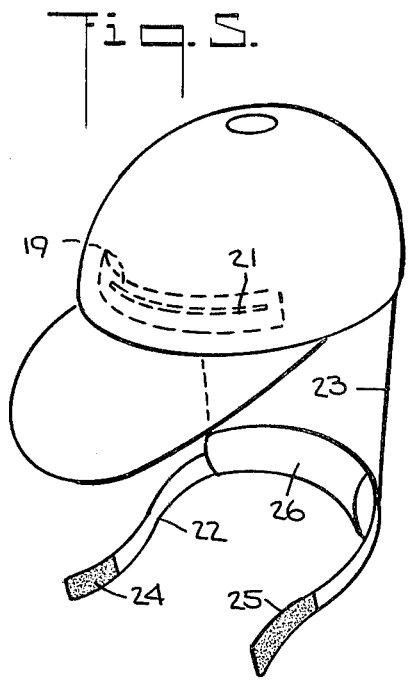
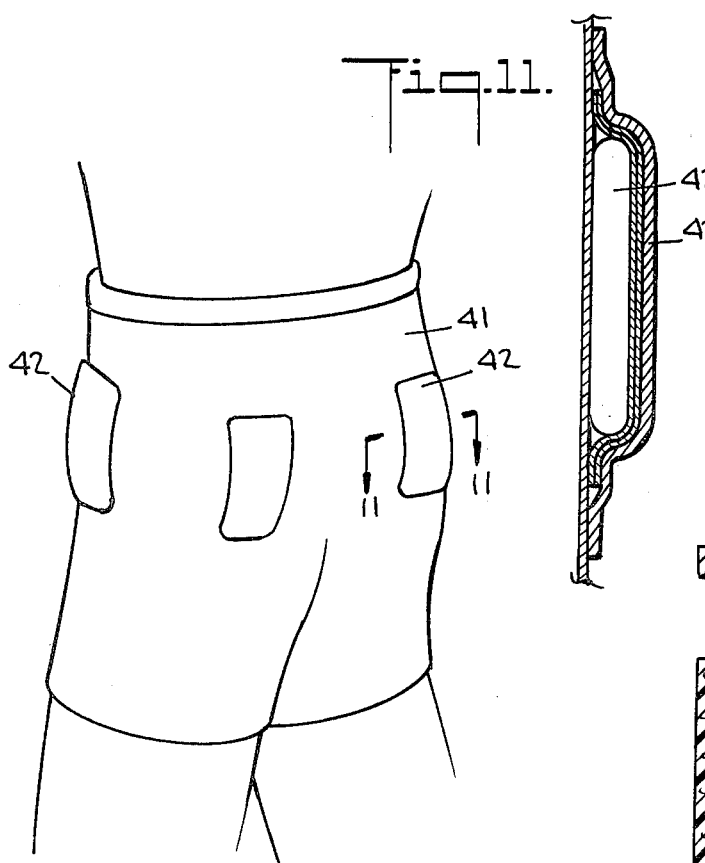
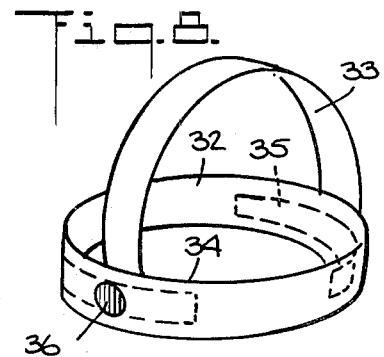
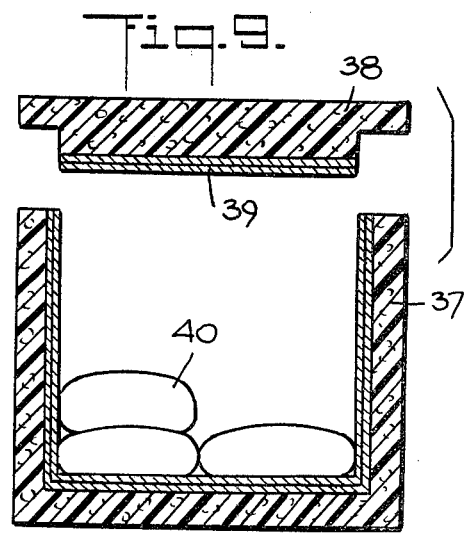

HEAT EXCHANGE SYSTEM FOR BODY SKIN

BACKGROUND OF INVENTION

This invention relates generally to a heat exchange system for personal use to provide beneficial cooling or warming effects, depending on the operating mode of the system, and more particularly to a system which includes replaceable thermal cartridges insertable in a fabric holder adapted to engage and conform to the skin of the user.

The interior of the human body has a normal temperature level which is usually said to be 98.6° F. But actually, in the course of each 24-hour period, the body temperature goes above and below this nominal value within a 1.8° F. range. Body temperature is determined by the relationship existing between the amount of heat internally generated, which depends on basal metabolism, and the amount of heat escaping from the body. Additional heat is produced as a result of muscular activity, this being dissipated by an increase in radiation, conduction or evaporation from the skin surface and by more rapid and deep breathing. Thus the skin is the interface between the internally heated body and the atmosphere, and is in heat exchange relationship therewith. If the heat produced by a body surpasses heat losses therefrom, this gives rise to fever; but if heat losses exceed heat production, then the body temperature falls below the nominal value, resulting in shivering and hypothermia.

The nerve centers for regulating body temperature are located in the forebrain region called the hypothalamus. When these nerve centers sense a decrease in blood temperature, they stimulate skeletal muscles to increase activity and they also stimulate the liver to enhance the expenditure of energy, thereby contributing heat to the blood. An increase in blood temperature causes the hypothalamus to call for the secretion of sweat and to route more blood to the skin areas, glandular activity of the liver then being inhibited and the general tonus of the skeletal muscles being lowered. These changes reduce body heat production and increase heat losses.

One can, to a limited degree, accommodate the body to widely different environmental conditions by appropriate clothing. Thus clothing providing good thermal insulation makes it possible for an individual to function effectively in severe cold. By wearing light, well-ventilated clothing, one can be reasonably comfortable in a hot climate.

Clothing, therefore, serves as a heat exchange function; for it determines the propagation rate of heat from the body to the atmosphere. When the ambient temperature is well below the body temperature, clothing acts as a thermal insulation to slow down the heat exchange rate and thereby reduce the loss of heat; and when the ambient temperature is well above body temperature, the rate at which heat is lost from the body is enhanced by suitable clothing, particularly if it acts as a wick to disperse sweat over a broad area to promote evaporative cooling.

There are, however, many situations where regardless of the clothing worn, the clothing is incapable of maintaining the body temperature at an acceptable level. Thus athletes, such as long-distance runners, tennis players and bicycle riders who exercise vigorously in warm environments may be subject to heat prostration, for they are unable to dissipate sufficient heat to maintain a safe body temperature. Even in a relatively cool indoor environment the athlete may sweat excessively, this giving rise to premature fatigue.

On the other hand, when an athlete exercises in a severely cold environment, the resultant increase in heat production may still be inadequate to overcome the rapid transfer of heat from the body to the atmosphere, particularly when the nature of the activity is such that the athlete cannot be heavily bundled in warm clothing.

Attempts have heretofore been made to couple a heat source or heat sink to the body in order to provide a cooling or warming effect. Thus the 1955 patent to Giardini, U.S. Pat. No. 2,715,315, discloses a wrist band which incorporates a dry ice pellet. Since the blood vessels are close to the surface of the wrist area, the device, according to Giardini, has a cooling effect on the entire body. The Amador U.S. Pat. No. 3,149,943 also shows a wrist band applicator, use being made of granular ammonium nitrate which is reacted with water to produce a cooling action. Henderson, U.S. Pat. No. 4,204,543, discloses a coolant band that encircles the head, use being made for this purpose of a freezable liquid. Merna, U.S. Pat. No. 3,465,120, shows a wrist applicator with an electrically-operated heating element.

While the devices disclosed in the above-identified patents seek to supply heat or cold to the body, they are relatively inefficient, for they fail to take into account certain physiological factors and they afford only a short-term cooling or heating action. For example, a battery-operated heater has an effective life that depends on the capacity of the battery. Since the capacity of a battery is related to its size and weight, a battery sufficiently compact to be carried on the person would necessarily have a small capacity.

Though some of these references make use of a gel which can be cooled to provide a heat sink, because this gel draws heat from the body, unless a large mass thereof is employed and the rate of heat transfer controlled, the cooling action of the gel is short lived.

SUMMARY OF INVENTION

In view of the foregoing, the main object of this invention is to provide a heat exchange system for personal use to effect beneficial cooling or warming effects for a prolonged period.

More particularly, the object of this invention is to provide a system which includes replaceable thermal cartridges which, when activated, are insertable in a fabric holder to form a thermal assembly adapted to engage and conform to the skin area, the activated cartridge functioning as a heat sink or heat source, depending on the selected operating mode.

A significant feature of the invention resides in the use of modular thermal cartridges, the system including means to store a supply of activated cartridges under thermally controlled conditions, so that when a cartridge is spent it may be quickly replaced. In this way the effective operating life of the system is not limited to one cartridge but is determined by the stored supply thereof.

By the term "activated cartridge," as used herein, is meant a cartridge enclosing a liquid or gel mass having a high heat capacity, which cartridge has been preheated or refrigerated to cause the entire mass to assume an elevated or reduced temperature, whereby the cartridge can then function as a heat source or heat sink when in engagement with the skin of a person.

Also an object of the invention is to provide a cartridge whose synthetic plastic film envelope has a metallic layer thereon acting to minimize thermal losses from the gel or liquid mass housed therein.

Still another object of the invention is to provide a fabric holder which includes a liquid crystal sensor making contact within the inserted activated cartridges to afford a color indication of the cartridge temperature.

A further object of the invention is to provide a relatively inexpensive system of the above type which operates efficiently and reliably.

Briefly stated, these objects are accomplished by a heat exchange system for personal use to provide beneficial cooling or warming effects, depending on the operating mode of the system. Included is a supply of replaceable thermal cartridges, each of which is insertable in a fabric holder having wicking properties, the loaded holder or thermal assembly being adapted to engage and conform to a skin area on the individual that is subject to sweating, such as the brow or neck. Each cartridge is constituted by a sealed flexible envelope formed of plastic film, preferably having a metallic layer thereon acting to reflect radiant energy. The envelope encloses a gel or liquid having a high heat capacity whereby when the supply of cartridges is pre-heated or refrigerated, each cartridge is thereby activated. When an activated cartridge is placed in the holder to engage the skin of an individual, it then functions either as a heat sink or heat source with respect thereto.

OUTLINE OF DRAWINGS

For a better understanding of the invention as well as other objects and further features thereof, reference is made to the following detailed description to be read in conjunction with the accompanying drawings, wherein:

FIG. 1 illustrates a hard hat which has a pair of thermal assemblies in accordance with the invention installed therein, the hat being shown in section;

FIG. 2 is a perspective view of the hard hat with one of the thermal assemblies removed therefrom;

FIG. 3 is a transverse section taken through one of the thermal assemblies;

FIG. 4 is a section view of a visored cap which incorporates a thermal assembly that is pressed against the brow of the wearer, the cap being associated with a neck yoke provided with a second thermal assembly;

FIG. 5 is a perspective view of the cap;

FIG. 6 illustrates, in perspective, an eyeshade which includes a thermal assembly;

FIG. 7 is a rear view of the eyeshade;

FIG. 8 illustrates, in perspective, a head band which incorporates front and rear thermal assemblies;

FIG. 9 is a sectional view of an insulation box for a supply of thermal cartridges;

FIG. 10 shows, in perspective, a pair of shorts having specialized pockets for storing a supply of thermal cartridges; and FIG. 11 is a transverse section taken in the plane indicated by line 11—11 in FIG. 10.

DESCRIPTION OF INVENTION

Hard Hat

Referring now to FIGS. 1, 2 and 3, there is shown a hard hat of conventional design which incorporates thermal assemblies 10 and 11 in accordance with the invention. The hat is constituted by a molded body 12 of synthetic plastic protective material, such as Kelvar, having a visor 13 integral therewith. The interior of the hat is provided with fabric webbing that includes a head band 14 which encircles the head of the wearer for accommodating the hat to the wearer's head size.

Each thermal assembly, as best seen in FIGS. 2 and 3, consists of a rectangular holder 15 within which is inserted a thermal cartridge 16. In practice, the holder dimensions may typically be 3 inches wide by 7 inches long. The thermal cartridge inserted in the holder has about the same dimensions.

Holder 15, which is formed of woven or non-woven textile material, is provided with a pair of straps 15A and 15B extending therefrom which terminate in the male component of a "Velcro" fastener. These straps loop about head band 14 and attach onto female Velcro components on holder 15 to secure the holder to the head band. The holder is also provided with an end opening having a "Velcro" fastener closure to permit quick insertion and removal of the cartridge. "Velcro" fasteners are constituted by an array of hook-shaped Nylon male elements which engage an array of female loops. A zipper or snap-button closure may be used for the same purpose.

The assemblies 10 and 11 are pressed, respectively, against the brow of the wearer and against the rear of the head adjacent the neck, the assemblies conforming to the skin surface in these regions of the body in heat exchange relation therewith.

The fabric material of the holder must be such as to minimize hot or cold shock by affording a degree of thermal insulation between the skin of the wearer and the thermal cartridge. At the same time, the fabric material must have good wicking properties so as to rapidly and efficiently absorb perspiration exuded from the skin and to disperse the absorbed perspiration over a broad area to promote evaporative cooling.

To this end, a textured fabric is used having these characteristics, such as a terry cloth fabric or one having similar towel-like properties. A preferred material is the Kaiser-Roth "Super Wick" terry cloth, a composite fabric consisting of 65% Orlon, 25% cotton and 25% Nylon. This material is exceptionally wickable and yet has good thermal insulating properties, serving to keep the activated thermal cartridge hot or cold, as the case may be, for a prolonged period.

The thermal cartridge 16 is constituted by a heat-sealed envelope of synthetic thermoplastic film material such as polyvinyl chloride, polypropylene or a polyester. A preferred polyester is "Mylar" which is flexible as well as tear and puncture resistant. The surface of the envelope is preferably aluminized by vacuum deposition, sputtering or other known techniques to provide a specular layer thereon of almost molecular thickness. This layer acts to reflect radiant energy emitted from within the cartridge, as well as radiant energy impinging thereon, thereby minimizing thermal energy leakage.

The cartridge is filled with a liquid or gel 17 having a high heat capacity. The gel may be of the type disclosed in the Spencer U.S. Pat. No. 3,885,403, which is constituted by a mixture of water, a freezing point depressant, such as glycerine or propylene glycol, and a suitable thickening agent. Also, a fungistat may be added to inhibit fungus growth.

In practice, a flexible strip consisting of a row of interconnected water-filled plastic cells may be inserted within the thermal cartridge, the strip being immersed in the gel. The water cells, when frozen, create a series of small ice blocks within the cartridge. This has the advantage of combining the heat of fusion characteristic of the ice with the higher heat capacity of the gel, thereby lengthening the effective cooling period of the cartridge when it operates in the cooling mode.

Also, instead of enclosing a gel in the sealed plastic envelope, the gel may be impregnated in a flexible foam pad which is inserted in the envelope to impart greater flexibility thereto than is obtainable from a mass of pure gel.

When the hard hat is intended to warm the wearer thereof, the cartridges are pre-heated in an oven until the gel therein is uniformly at the desired elevated temperature. The activated cartridges are then inserted in the fabric holders and attached to the head band, as shown in FIG. 1, to impart to the wearer a warming effect that will last approximately one-half hour or more.

When the hard hat is intended to cool the wearer thereof, the cartridges are first refrigerated, the activated cartridges being then inserted in the holders to cool the wearer for about one-half an hour or so. The rate of heat transfer and hence the effective life of the cartridge are governed by the fabric holders, as will be later explained.

Because the thermal assemblies are pressed against the forehead and the area just above the neck, they have the greatest influence on the thermal comfort as perceived by the wearer, for these are the body areas where the most heat can be extracted or added. It is to be noted in this regard that the head, in order to promote constant blood flow to the brain, possesses few arteries that vasco-constrict or vasco-dilate in the presence of heat or cold.

The activated assemblies on the hard hat, when spent, are replaced by activated assemblies taken from a portable supply thereof so as to provide a heat transfer system capable of cooling or heating the user for a relatively prolonged period. While the thermal assemblies are shown as being connectable to the head band of the hard hat, the fabric holders may be permanently sewn or otherwise joined to the head band.

Visored Cap

Referring now to FIGS. 4 and 5, there is shown a visored cap having a fabric holder 19 sewn therein adapted to receive a thermal cartridge 20 to provide a thermal assembly which is pressed against the forehead of the wearer. To this end, the fabric holder, instead of being end-loaded as in the hard hat, is provided at its rear face with a longitudinal slit 21 having a Velcro closure, making it easier to quickly load the holder.

In addition, cap 18 is provided with a neck yoke 22 which is linked to the rear of the cap by a strap 33. Neck yoke 22 is provided at its extremities with male and female Velcro fastener components 24 and 25, so that the yoke can be secured about the neck. Yoke 22 is provided with a thermal assembly 26 which is essentially the same as the forehead assembly.

As pointed out previously, the two most sensitive body areas for thermal exchange are the forehead and neck; hence the cap embodiment shown in FIGS. 4 and 5 provides an assembly at both highly-sensitive sites.

Eyeshade

The arrangement shown in FIGS. 6 and 7 is that of an eyeshade 27 which is held to the head of the wearer by an elastic loop 28. This eyeshade incorporates a fabric holder 29 having a rear slit 30 for receiving a thermal cartridge TC which is pressed against and conforms to the forehead of the wearer.

Mounted on the front face of fabric holder 29 at the center thereof is an encapsulated liquid crystal cell 31 of the heat-responsive chromatic type which exhibits a color which depends on the prevailing temperature.

Cell 31 is preferably of the type disclosed by NCR Corporation in its booklet "Chameleon-Brand of Encapsulated Liquid Crystal," as well as the references cited therein. This cell makes use of thermally-sensitive compounds that are normally gray or colorless in appearance and change in color within a given temperature range, from red at the lower end portion of the range through yellow and green to blue at the high end portion of the range. Thus the color displayed is indicative of the prevailing temperature.

One can, as noted in the NCR booklet, design the liquid crystal composition so that the color spectrum is related to a specified temperature range. Thus for use in the context of the present invention, the liquid crystal may be designed so that when it turns green, the cartridge is at its proper activated temperature, and when it turns red or yellow, it has ceased to be acceptably active.

Head Band

A simplified version is shown in FIG. 8, which takes the form of an elastomeric head band 32 to encircle the head of the wearer with a crown loop 33, the band having a front thermal assembly 34 secured thereto which follows the curvature of the forehead and a rear thermal assembly 35 which engages the back of the head.

In addition, a chromatic liquid crystal cell 36 is fitted at the center front of the head band. This head band slips easily over the head of the wearer and conforms thereto. The band itself is preferably made of a fabric having good wicking properties.

Storage

In the heat exchange articles of apparel shown in FIGS. 1 to 8, the thermal assemblies in contact with the wearer's skin are capable of remaining active for about a half hour to 45 minutes. In a system in accordance with the invention, a portable supply of activated cartridges must be provided, so that when the cartridges being worn cease to be effective, they can be quickly replaced with fully charged or activated cartridges to prolong the desired cooling or heating effect.

To this end, as shown in FIG. 10, a portable, thermally-insulated box 37 is provided, a foam plastic material such as styrofoam being incorporated in the walls of the box. Box 37 includes a thermally-insulated removable lid 38. The inner walls of the box are lined with multiple layers 39 of metallized Mylar film so that the box functions, as it were, as a "Thermos" container to maintain the stored cartridges in their activated state for a prolonged period, such as four or more hours.

Stored within the box is a supply of cartridges 40. When the cartridges are intended to operate in the heating mode, these cartridges are pre-heated in an oven, the container serving to hold the activated cartridges for several hours in this state. When the activated cartridges are to operate in a cooling mode, they may be pre-refrigerated. In addition, a refrigerant such as a block of dry-ice may be placed within the box. It is sufficient in some cases to merely place a frozen food product, such as a can of frozen juice, in the box to maintain the cartridges therein in the cold state.

Another approach to providing a supply of activated cartridges, say, for a tennis player, is to equip a pair of playing shorts 41, as shown in FIG. 10, with specialized front and rear pockets 42, each holding one or several activated cartridges 43. These pockets are preferably formed of thermal insulating fabric lined with metallized Mylar film in multiple layers, so that each pocket serves as a refrigeration compartment. Thus the player wearing these special shorts carries on his person a supply of activated cartridges sufficient for several hours of play.

Operating Procedures

In using thermal assemblies in accordance with the invention, it is desirable before attaching each assembly to the hard hat or whatever other article is worn by the user, to wet the fabric of the holder. This makes possible evaporative cooling for several minutes (5 to 10), and it also enhances the thermal conductivity of the holder.

For this purpose, one may furnish the user with a small refillable syringe or pen acting as a water gun or squirter to wet down the fabric when the sensation of cooling begins to fade. This extends the cooling time; for as the activated cold cartridge proceeds to discharge and the temperature differential between the cartridge and the skin then diminishes, it becomes more difficult to effect heat transfer through the insulating fabric. By slightly wetting the fabric holder, an increased conduction path is established between the skin and cartridge. The water spray has the effect of reducing the thermal insulating characteristics of the fabric at a time when it is most needed. Some portable means of spraying water on the fabric therefore puts into the hands of the user the ability to effectively vary the thermal insulating characteristics of the fabric layer interposed between the thermal cartridge and the skin.

When the assembly functions in the cooling mode and the thermal cartridge is activated to assume a uniform internal temperature of, say, 32° F., operation of the assembly in the preferred manner passes through four distinct phases. In the first phase, which lasts about 5 to 10 minutes, the wetted fabric holder pressed against the skin of the user gives rise to evaporative cooling. In the second phase, which begins when most of the water has evaporated, cooling is effected for about 30 to 45 minutes by conductive heat transfer from the cold cartridge (32° F.) to the much warmer skin. Because of the large temperature differential that then exists, the heat transfer rate is fairly rapid, and the user, therefore, has the marked sensation of a significant heat loss. At the beginning of the second phase when the fabric is still damp to enhance the thermal conductivity thereof, but such conductivity diminishes as the fabric dries, thereby slowing down the transfer rate and extending the effective life of the activated cartridge.

In the third phase toward the end of the 45-minute second phase interval, the cartridge is now approaching the de-activated state. At this point, the insulating properties of the fabric holder acts to slow down the rate of heat transfer from the now semi-warm cartridge to the skin. One may then at the point use a water squirter to wet the fabric to improve conductivity and thereby extract, as it were, the remaining 10 to 15% of the stored heat capacity in the cartridge.

In the fourth and final phase, the cartridge is now fully de-activated, and the wicking fabric of the holder then switches to the evaporative cooling mode, for the user (assuming a player who is exercising strenuously) now perspires freely, the perspiration being rapidly drawn from the skin by the fabric.

While there has been shown and described a preferred embodiment of heat exchange system for body skin in accordance with the invention, it will be appreciated that many changes and modifications may be made therein without, however, departing from the essential spirit thereof. Thus while the thermal assemblies have been shown in conjunction with head and neck pieces of various sorts, the invention is not limited to such articles of apparel, and the thermal assemblies may be incorporated in shirts, shorts, belts, gloves, wristbands and in other articles which make contact with the skin so as to provide a cooling or warming action, as desired, including anklets and girdles. To accelerate heating of the cartridges, they may be immersed in boiling water rather than being placed in an oven.

I claim:

1. A heat exchange system for personal use in the field to provide cooling effects, said system comprising:
   (A) an article of head apparel having an inner zone that encircles the head of the wearer; and
   (B) a flexible thermal assembly interposed between a portion of the inner zone and the skin to conform to the contour of the skin, said assembly being constituted by a holder formed of a fabric having good wicking properties and a replaceable cartridge inserted therein formed by a sealed flexible envelope of synthetic plastic film material enclosing a gel having a much lower freezing point than water, and water-filled plastic cells immersed in said gel to create, when frozen, ice blocks within the cartridge, thereby combining the heat of fusion characteristic of the ice with the higher cooling capacity of the gel to lengthen the effective cooling period of the cartridge, said cartridge being activatable to cause said mass to assume a uniform cold temperature; and
   (C) a portable storage device containing a supply of pre-activated cartridges making it possible to replace deactivated cartridges in the field.

2. A system as set forth in claim 1, wherein said article is a hard hat having interior webbing including a fabric head band that encircles the head of the wearer and thermal assemblies secured to the front and rear of the head band.

3. A system as set forth in claim 2, wherein said fabric holder includes a pair of straps which loop about the head band to secure the assembly thereto.

4. A system as set forth in claim 1, wherein said envelope film has a metallized layer thereon providing a specular surface to reflect radiation.

5. A system as set forth in claim 1, wherein said article of apparel is a head band having front and rear thermal assemblies secured thereto.

6. A system as set forth in claim 1, wherein said apparel is an eyeshade having a thermal assembly secured thereto to engage the brow of the wearer.

7. A system as set forth in claim 6, wherein said eyeshade has a liquid crystal chromatic cell secured thereto to indicate the prevailing temperature of the cartridge.

8. A system as set forth in claim 1, wherein said apparel is a visored cap having an assembly secured thereto to engage the brow of the wearer.

9. A system as set forth in claim 8, wherein said cap has a neck yoke linked thereto having a second assembly thereon to engage the neck of the wearer.

10. A system as set forth in claim 1, wherein said holder has an end opening provided with a closure.

11. A system as set forth in claim 1, wherein said holder has a longitudinally-extending rear opening provided with a closure.

12. A system as set forth in claim 1, wherein said storage device is a thermally insulated box for housing a plurality of activated cartridges.

13. A system as set forth in claim 1, wherein said fabric is a composite of Orlon, cotton and Nylon.

14. A system as set forth in claim 1, wherein said assembly is placed at the rear of the head against the neck of the wearer.

* * * * *